United States Patent [19]

Patterson

[11] Patent Number: 5,461,078
[45] Date of Patent: Oct. 24, 1995

[54] ANTI-CANCER COMPOUNDS

[75] Inventor: Laurence H. Patterson, Glenfield, England

[73] Assignee: British Technology Group Limited, London, United Kingdom

[21] Appl. No.: 133,033

[22] Filed: Apr. 10, 1992

[86] PCT No.: PCT/GB92100646

§ 371 Date: Oct. 22, 19923

§ 102(e) Date: Oct. 22, 1993

[30] Foreign Application Priority Data

Apr. 12, 1991 [GB] United Kingdom .................. 9107843

[51] Int. Cl.$^6$ ........................ C07C 291/04; A61K 31/13
[52] U.S. Cl. .......................... 514/644; 514/641; 564/270; 564/299
[58] Field of Search .................................. 564/299, 270; 514/641, 644

[56] References Cited

U.S. PATENT DOCUMENTS

| | | |
|---|---|---|
| 3,174,994 | 3/1965 | Sutton . |
| 4,686,218 | 8/1987 | Marinis et al. . |
| 4,963,554 | 10/1990 | Combs et al. . |

FOREIGN PATENT DOCUMENTS

| | | |
|---|---|---|
| 254224A | of 1968 | European Pat. Off. . |
| 0103381 | 3/1984 | European Pat. Off. . |
| 0138302 | 4/1985 | European Pat. Off. . |
| 0145226 | 6/1985 | European Pat. Off. . |
| 254224A1 | of 1988 | European Pat. Off. . |
| 1118414 | of 1956 | France . |
| 1316453 | of 1962 | France . |
| 1942185 | 8/1968 | Germany . |
| 3405330A1 | of 1985 | Germany . |
| WO91/05824 | 5/1991 | WIPO . |

OTHER PUBLICATIONS

J. Med. Chem., 1989, 24, Karzhendler et al. "Synthesis of aminoanthraquinone . . . ", pp. 23–30.
Stefanska, et al "Synthesis of Unsymmetrically . . . " J. Med. Chem. 1989 32, pp. 1724–1728.
Cheng et al. "The Design, Synthesis . . . " Progress in Medicinal Chemistry, 1983, 20. pp. 83–118.
Fujiwara et al. "N–Oxides and . . . " J. Het. Chem. 1969, 6 pp. 389–392.
Langendoen et al. "An approach to novel . . . " Tetrahedron, 1988, 44, pp. 3627–3631.
Langendoen et al. "Regiospecific C–9 substitution . . . " Terahedron, 1989, 45, pp. 1759–1762.
Brunston et al. "Alcaloides Des . . . " Photochemistry, 1972, 11, pp. 3073–3075.
Bild et al. "Notiz uber die . . . " Helvetica Chimica Acta, 1967, 50, pp. 1885–1892.
Jarman et al. "Analogues of tamoxifen . . . " Anti–Cancer Drug Design, 1986, 1 pp. 259–268.
Zeman et al. "SR–4233: A new bioreductive agent" Int. J. Radiation Oncology, Biol. Phys., 1986, 12, pp. 1239–1242.
Jenkins. "Hypoxia–selective agents . . . " The Chemistry of Antitumor Agents, Wilman (eds.), 1990, pp. 342–369.
Hulbert et al. "Hycanthone analogs . . . " Science, 1974, 186 pp. 647–648.
Connary. "Alkylating prodrugs in . . . " Structure–Activity Relationship of Anti–tumor Agents, 1983, pp. 47–57.
Wilson et al. "Bis–Bioreductive agents . . . " 7th Intl Conf. on Chem. Modifiers of Cancer Treatment, Florida, USA, Feb. 2–5, 1991, p. 248.
Proceedings, 83rd Annual Meeting of the American Association for Cancer Research, May 20–23, 1992, San Diego, Calif., USA, vol. 33, Mar. 1992.
NCI–EORTC symposium on new drugs in cancer therapy. Amsterdam, Mar. 17–20, 1992.
A. P. Krapcho et al. "Synthesis and antitumor . . . " J. Med. Chem. 1991, 34 pp. 2373–2380.

Primary Examiner—Robert Gerstl
Attorney, Agent, or Firm—Nixon & Vanderhye

[57] ABSTRACT

Compounds of formula (I)

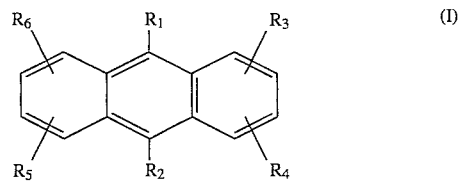

in which $R_1$ is CH=CHR, CH=NNHR, CH=N—A—N(O)R'R" or $CH_2$—NH—A—N(O)R'R" and $R_2$ is separately selected from hydrogen, CH=CHR, CH=NNHR, CH=N—A—(O)R'R" and $CH_2$—NH—A—N(O)R'R", wherein A is a $C_{2-4}$ alkylene group with a chain length between N or NH and N(O)R'R" of at least 2 carbon atoms, R is a thiazolyl or imidazolyl group in which the tertiary nitrogen atom is in N-oxide form, and R' and R" are each separately selected from $C_{1-4}$ alkyl groups and $C_{2-4}$ hydroxyalkyl and $C_{3-4}$ dihydroxyalkyl groups in which the carbon atom attached to the nitrogen atom does not carry a hydroxy group and no carbon atom is substituted by two hydroxy groups, or R' and R" together are a $C_{2-6}$ alkylene group which with the nitrogen atom to which R' and R" are attached forms a heterocyclic group having 3 to 7 atoms in the ring, and $R_3$, $R_4$, $R_5$ and $R_6$ are each separately selected from hydrogen, hydroxy, halogeno, amino, $C_{1-4}$ alkoxy and $C_{2-8}$ alkanoyloxy, and physiologically acceptable salts thereof are of value in the treatment of cancer.

10 Claims, No Drawings

ANTI-CANCER COMPOUNDS

This application is a 371 of PCT/GB92/00646 filed Apr. 4, 1992.

This invention relates to novel anthracenes which are of particular value in the treatment of cancer.

Certain aminoalkylamino anthracenes have been described for use as chemotherapeutic agents for the treatment of cancer. However, in common with other cytotoxic chemotherapeutic agents these anthracenes have the disadvantage that their activity is not confined to neoplastic cells and they therefore exhibit various undesirable side effects.

It is an object of the present invention to provide a group of anthracene pro-drugs which are of lesser cytotoxicity than the drug itself, preferably being substantially non-cytotoxic, the pro-drugs being converted in vivo under the anaerobic conditions within neoplastic tissue to the cytotoxic drug thereby mitigating the side effects of administering that drug directly.

Accordingly the present invention comprises a compound of formula (I)

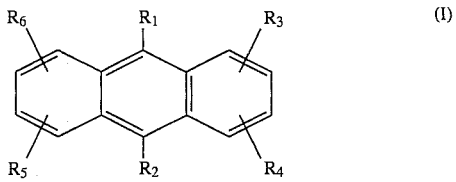

in which $R_1$ is CH=CHR, CH=NNHR, CH=N—A—N(O)R'R" or $CH_2$—NH—A—N(O)R'R" and $R_2$ is separately selected from hydrogen, CH=CHR, CH=NNHR, CH=N—A—(O)R'R" and $CH_2$—NH—A—N(O)R'R", wherein A is a $C_{2-4}$ alkylene group with a chain length between N or NH and N(O)R'R" of at least 2 carbon atoms, R is a thiazolyl or imidazolyl group in which the tertiary nitrogen atom is in N-oxide form, and R' and R" are each separately selected from $C_{1-4}$ alkyl groups and $C_{2-4}$ hydroxyalkyl and $C_{3-4}$ dihydroxyalkyl groups in which the carbon atom attached to the nitrogen atom does not carry a hydroxy group and no carbon atom is substituted by two hydroxy groups, or R' and R" together are a $C_{2-6}$ alkylene group which with the nitrogen atom to which R' and R" are attached forms a heterocyclic group having 3 to 7 atoms in the ring, and $R_3$, $R_4$, $R_5$ and $R_6$ are each separately selected from hydrogen, hydroxy, halogeno, amino, $C_{1-4}$ alkoxy and $C_{2-8}$ alkanoyloxy, the compound optionally being in the form of a physiologically acceptable salt.

The compounds of formula (I) contain at least one tertiary nitrogen atom in N-oxide form. Anti-cancer drugs containing a group of this type are not unknown. However, although anthracene drugs have been described for various uses, we are not aware of any previous disclosure of anthracene anti-cancer drugs which contain a tertiary nitrogen atom in N-oxide form. Moreover, the N-oxide compounds of the present invention have the particualr value that they are pro-drugs of lower cytotoxicity which generate a toxic drug in vivo. Thus, it is believed that the N-oxides of the present invention are bioreductively activated within neoplastic tissue to form the cytotoxic compound containing the tertiary nitrogen atom without the oxide atom, thereby providing the desired anti-cancer activity of this compound but with mitigation of its undesired side effects.

A similar approach to that of the present invention is described for aminoalkylamino anthraquinones in UK Patent Application No. GB 2237283 and PCT Application No. GB 90/01574.

As regards groups $R_1$ and $R_2$ of the type CH=CHR and CH=NNHR, R is preferably a 1,3-thiazolyl N-oxide group or more especially an imidazolyl N-oxide group and is preferably attached to CH=CH— or CH=NNH— at the 2-position of the ring system. Of the two types of group, CH=NNHR groups are particularly preferred, especially the group

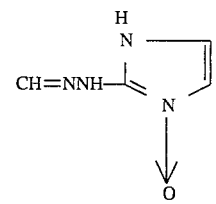

Although such groups CH=CHR and CH=NNHR are of some interest, groups $R_1$ and $R_2$ of the type CH=N—A—N(O)R'R" and especially $CH_2$—NH—A—N(O)R'R" are particularly preferred. The group A present in such groups (which may differ among the groups $R_1$ and $R_2$) may be branched or more conveniently a straight chain alkylene group, i.e. tetramethylene, especially trimethylene, or particularly ethylene.

R' and R" (which again may differ among the groups $R_1$ and $R_2$) may also have a branched carbon chain but are conveniently straight chain whether they are alkyl groups or hydroxy-substituted alkyl groups. When R' or R" is a monohydroxyalkyl group this is conveniently substituted terminally and when R' or R" is a dihydroxyalkyl group this will be substituted terminally by one of the hydroxy groups for a $C_3$ group and conveniently is also so substituted for a $C_4$ group. When R' and R" are alkyl the preference is for a group of three or especially two or one carbon atoms and when R' and R" are hydroxy-substituted alkyl the preference is for the alkyl group to be of three carbon atoms or, in the case of a monohydroxyalkyl group, alternatively of two carbon atoms. Examples of preferred individual groups R' and R" are $CH_2CH_2CH_3$, $CH_2CH_2OH$, $CH_2CH_2CH_2OH$, $CH(CH_3)CH_2OH$ and $CH_2CHOHCH_2OH$, and especially $CH_3$ and $CH_2CH_3$. Whilst R' and R" will more usually be identical there can be certain advantages as indicated hereinafter in having non-identical groups R' and R".

Alternatively R' and R" together with the nitrogen atom to which they are attached may represent a heterocyclic group —$N(CH_2)_n$ where n is 2 to 6, i.e. aziridin-1-yl, azetidin-1-yl, pyrrolidin-1-yl, piperidin-1-yl and perhydroazepin-1-yl, the smaller groups such as azetidin-1-yl and especially aziridin-1-yl being of most interest.

Specific groups CH=N—A—N(O)R'R" of particular interest are CH=N—$(CH_2)_2$—N(O) $(CH_3)C_2H_5$, CH=N—$(CH_2)_2$—N(O)(CH $_2CH_2OH)_2$, CH=N—$(CH_2)_2$—N(O)($CH_2CH_2CH_2OH)_2$, CH=N—$(CH_2)_2$—N(O)($CH(CH_3)CH_2OH)_2$, CH=N—$(CH_2)_2$—N(O)($CH_2CHOHCH_2OH))_2$, especially CH=N—$(CH_2)_2$—N(O)$(CH_3)_2$ and CH=N—$(CH_2)_2$—N(O)$(C_2H_5)_2$, and also the corresponding groups in which —$(CH_2)_2$— is replaced by —$(CH_2)_3$—.

Specific groups $CH_2$—NH—A—N(O)R'R" of particular interest are $CH_2$—NH—$(CH_2)_2$—N(O)$(CH_3)C_2H_5$, CH$_2$—NH—$(CH_2)_2$—N(O)$(CH_2CH_2OH)_2$, $CH_2$—NH—$(CH_2)_2$—N(O)$(CH_2CH_2CH_2OH)_2$, CH $_2$—NH—$(CH_2)_2$—N(O)$(CH(CH_3)CH_2OH)_2$, $CH_2$—NH—$(CH_2)_2$—N(O)$(CH_2CHOHCH_2OH)_2$, especially $CH_2$—NH—$(CH_2)_2$—N(O)$(CH_3)_2$ and $CH_2$—NH—$(CH_2)_2$—N(O)$(C_2H_5)_2$, and also the corresponding groups in which —$(CH_2)_2$— is replaced by —$(CH_2)_3$—.

Halogeno groups $R_3$ to $R_6$ may be fluoro, chloro, bromo or iodo but are preferably bromo and especially chloro. Alkoxy and alkanoyloxy groups $R_3$ to $R_6$ may be branched or especially straight chain and are conveniently of 1 or 2 carbon atoms for the alkoxy groups and of 2 or 3 carbon atoms for the alkanoyloxy groups. Specific examples of groups $R_3$ to $R_6$ are hydroxy, chloro, amino, methoxy, ethoxy, acetyloxy and propionyloxy. However some groups such as hydroxy groups are of lesser interest than others.

Formula (II) illustrates the system used for numbering the various positions of the anthracene ring system.

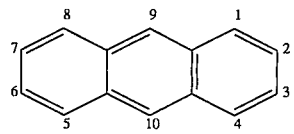

It will be seen from this formula that when $R_1$ and $R_2$ are identical certain of positions 1 to 8 are equivalent, and this is also true for a smaller number of positions even when $R_1$ and $R_2$ are not identical. Preferences as to positions of substitution are expressed herein by identifying groups $R_3$ to $R_6$ which are other than hydrogen in the order $R_3, R_4, R_5, R_6$ and, as is conventional practice, by identifying substituted positions in the order 1, 2, 3, 4, 5, 6, 7, 8. Thus, for example, a compound in which $R_1$ and $R_2$ are identical having one substituent only at a ring position nearest to one of these groups is identified as having that substituent as a group $R_3$ at position 1 and groups $R_4, R_5$ and $R_6$ which are hydrogen.

It is preferred that $R_2$ is other than hydrogen so that both of the 9 and 10 positions are substituted by a group selected from CH=CHR, CH=NNHR, CH=N—A—N(O)R'R" and $CH_2$—NH—A—N(O)R'R", the two substituents $R_1$ and $R_2$ conveniently being the same one of these four types and preferably being identical.

The compounds (I) may contain from one to four substituent groups $R_3$ to $R_6$. The groups $R_3$ and $R_4$ may be at any of positions 1, 2, 3 and 4 and the groups $R_5$ and $R_6$ may be at any of positions 5, 6, 7 and 15 but the positions 1, 4, 5 and 8 are of most interest. However, at least $R_4$ and $R_6$ are preferably hydrogen and in many instances each of $R_3, R_4, R_5$ and $R_6$ is hydrogen.

Compounds of particular interest thus have one of:

(1) $R_1=CH_2$—NH—A—N(O)R'R", $R_2=R_3=R_4=R_5=R_6=$H;

(2) $R_1=R_2=CH_2$—NH—A—N(O)R'R" (conveniently being identical groups), $R_3=R_4=R_5=R_6=$H;

(3) $R_1$=CH=CHR or CH=NNHR, $R_2=R_3R_4R_5=R_6=$H;

(4) $R_1=R_2$=CH=CHR or CH=NNHR (conveniently being identical groups), $R_3=R_4=R_5=R_6=$H.

Of these, the compounds of types (2) and (4) are preferred, particularly when $R_1$ and $R_2$ are identical.

Specific compounds according to the present invention include those compounds of types (1) and (2) just listed in which the or each group $CH_2$—NH—A—N(O)R'R" has a group A which is $(CH_2)_3$ or particularly $(CH_2)_2$ and groups R' and R" which are each separately $CH_3$, $CH_2CH_2CH_3$, $CH_2CH_2OH$, $CH_2CH_2CH_2OH$, $CH(CH_3)CH_2OH$ or $CH_2CHOHCH_2OH$ or particularly $CH_2CH_3$. Preferably R' and R" are identical for each group $CH_2$—NH—A—N(O)R'R" and conveniently where two groups $CH_2$—NH—A—N(O)R'R" are present these are identical.

A further group of specific compounds according to the present invention includes those compounds of types (3) and (4) listed hereinbefore in which $R_1$ or $R_1$ and $R_2$, which are conveniently identical, are selected from

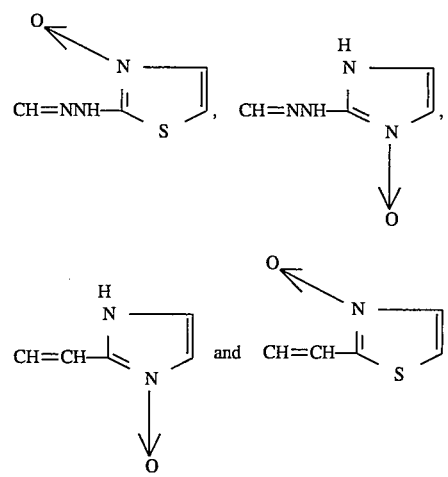

Of these the first three groups are of greatest interest.

Particularly preferred specific compounds are those of formulae (III) and (IV) and the analogues of (III) in which the two methyl groups in $N(O)(CH_3)_2$ are replaced by two n-propyl, 2-hydroxyethyl, 2-hydroxypropyl, 3-hydroxypropyl, 2,3-dihydroxypropyl or particularly ethyl groups, such compounds being in the free base or a salt form.

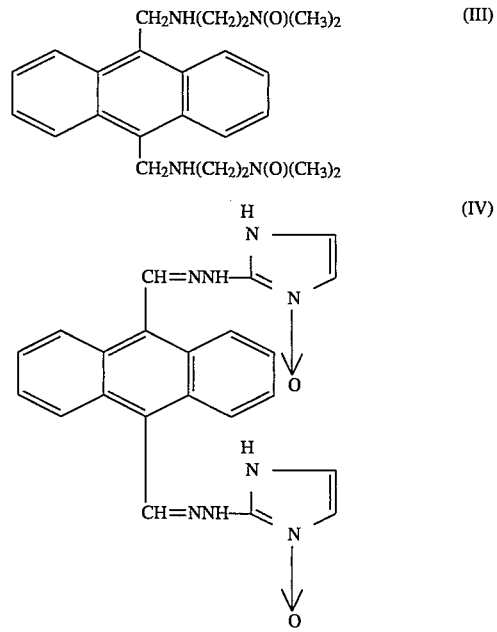

Certain substituents in the compounds (I) may contain one or more asymmetric carbon atoms and the compounds will then exist in stereoisomeric forms. Moreover, in the case where R' and R" are different this will introduce a centre of asymmetry at the nitrogen atom in N-oxide form. It will be appreciated that one stereoisomeric form of a compound may be of particular interest by virtue of advantageous physical properties, for example greater solubility, or biological activity, for example by virtue of greater ease of enzymic reduction.

As indicated the compounds (I) may be used in the form of a physiologically acceptable salt which will be an acid addition salt with an organic or inorganic acid. Examples of such inorganic acids are hydrochloric, hydrobromic, hydroiodic, phosphoric and sulphuric. Examples of such organic acids are acetic, ascorbic, benzoic, citric, fumaric, gluconic, isethionic, lactic, maleic, malic, methane sulphonic, oxalic, succinic, sulphamic and tartaric. Of these the hydrohalic acids and especially hydrochloric acid are of particular interest. Although the salts will usually have similar physiological properties to the free base they may have the advantage of enhanced solubility, etc.

The compounds (I) may conveniently be prepared through the oxidation of the tertiary amino group(s) of the corresponding compound in which each group CH=CHR, CH=NNHR, CH=N—A—N(O)R'R" and CH$_2$—NH—A—N(O)R'R" in the compound (I) is instead a corresponding group in which N replaces N(O). Thus, for example, anthracenes containing various [2-(dialkylamino)ethyl]amino, {2-[di-(hydroxyalkyl)amino]ethyl}amino and [2-(cyclic alkyleneamino)ethyl]amino groups may be oxidized to the ω-N-oxides and the tertiary nitrogen atoms of thiazole or imidazole rings may be converted to N-oxide form. Where appropriate the precursor compound which is oxidized may contain one or more modified groups R, R', R", R$^3$, R$^4$, R$^5$ and R$^6$ as compared with the parent compound, the groups corresponding to those in the compound (I) being generated from the modified groups after the oxidation has been effected. In general, however, it is desirable that the precursor corresponds to the final compound apart from the presence of N instead of N(O).

Any suitable oxidizing agent for converting a tertiary aliphatic amine to N-oxide form may be used, for example aqueous hydrogen peroxide/methanol (Foster et al, Biochem. Pharmacol., 1980, 29, 1977), oxone (potassium peroxymonosulphate) (Kennedy et al, Journal of Organic Chemistry, 1960, 1901), tetra-n-butylammonium octamolybdate (Jarman et al, Anti-Cancer Drug Design, 1986, 1, 259), and a peracid such as m-chloroperbenzoic acid (Craig et al, Journal of Organic Chemistry, 1970, 35, 1721). The last mentioned reagent is preferred, reaction at room temperature or a lower temperature down to −70° C. in the dark overnight with an excess of such an acid is usually sufficient to effect conversion to the N-oxide.

Where the compound (I) can exist in d and l forms as well as the dl form an optically active isomer may be synthesised either substantially free from these other forms, or at least in a major proportion by weight as compared with them, either by using optically active reagents in the synthesis of the compound or, particularly in the case of the optically active compounds in which R' and R" are different, by resolving the dl form, especially by using an optically active inorganic or organic acid to provide two stereoisomeric salts with different physical properties. In such an instance and also where the compound (I) is used in the form of a salt the salt may be prepared by reaction of the organic base (I) with the appropriate inorganic or organic acid according to conventional procedures, usually by simple admixture in solution. The acid addition salts are generally crystalline solids which are relatively soluble in water, methanol, ethanol and similar solvents.

Accordingly the present invention comprises a process for the preparation of a compound of formula (I) as defined hereinbefore which comprises oxidizing a compound of formula (Ia)

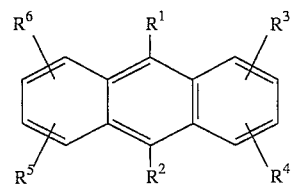

in which $R^1$, $R^2$, $R^3$, $R^4$, $R^5$ and $R^6$ correspond to $R_1$, $R_2$, $R_3$, $R_4$, $R_5$ and $R_6$, respectively, in the compound (I) but with each of the groups of the type CH=CHR, CH=NNHR, CH=N—A—N(O)R'R" and CH$_2$—NH—A—N(O)R'R" in the compound (I) being instead the corresponding group with N replacing N(O) in the compound (Ia) and one or more groups R', R", $R^3$, $R^4$, $R^5$ and $R^6$ in the compound (Ia) optionally instead being in a form convertible to said group or groups present in the compound (I), and where appropriate converting the one or more so modified groups R', R", $R^3$, $R^4$, $R^5$ and $R^6$ in the compound (Ia) to the form present in the compound (I) and/or forming an acid addition salt with a physiologically acceptable organic or inorganic acid.

Various routes are available for the synthesis of the intermediates which are oxidized to the compounds (I) of the present invention as will be apparent to the man skilled in the art from the literature, for example, procedures such as those described in various of the literature references of Chapters 1 and 2, in particular, of The Chemistry of Antitumour Agents, 1990, Wilman (editor), published by Blackie (London) and Chapman and Hall (New York) or modifications of those procedures. Examples of particular literature references are Murdock et al, Journal of Medicinal Chemistry, 1982, 25, 505–518 and Wunz et al, Journal of Medicinal Chemistry, 1987, 30, 1313–1321.

Where one or more substituents $R_3$ to $R_6$ is present in the compound (I) it may be appropriate, depending on the route of synthesis, to have these present throughout in their final form or to generate the desired groups at a later stage in the synthesis. Ether and ester groups may of course readily be prepared by modification of hydroxy groups according to known procedures, precursors containing a hydroxy group X more often being described in the literature than those containing a corresponding ether or ester substituent.

Certain of the intermediates of formula (Ia) corresponding to compounds (I) described herein but without the tertiary amine group(s) in N-oxide form are novel and are within the scope of this invention.

The compounds (I) may be formulated with a physiologically acceptable diluent or carrier for use as pharmaceuticals for both veterinary, for example in mammals, and particularly human use by a variety of methods. For instance, they may be applied as a composition incorporating a liquid diluent or carrier, for example an aqueous or oily solution, suspension or emulsion, which may often be employed in injectable form for parenteral administration and therefore may conveniently be sterile and pyrogen free. Oral administration may also be used and although compositions for this purpose may incorporate a liquid diluent or carrier, it is more usual to use a solid, for example a conventional solid carrier material such as starch, lactose, dextrin or magnesium stearate. Such solid compositions may take the form of powders but are more conveniently of a formed type, for example as tablets, cachets, or capsules (including spansules). Alternative, more specialized types of formulation include liposomes and nanoparticles.

Other types of administration than by injection or through the oral route which are of use in both human and veterinary contexts include the use of suppositories or pessaries.

Another form of pharmaceutical composition is one for buccal or nasal administration. Other formulations for topical administration include lotions, ointments, creams, gels and sprays.

However, in the treatment of cancer parenteral and sometimes topical administration is often of particular interest.

Compositions may be formulated in unit dosage form, i.e. in the form of discrete portions containing a unit dose, or a multiple or sub-unit of a unit dose.

Whilst the dosage of the compound used will vary according to the activity of the particular compound and the condition being treated, it may be stated by way of guidance that a dosage selected in the range from 0.1 to 20 mg/kg of body weight per day, particularly in the range from 0.1 to 5 mg/kg of body weight per day, will often be suitable. However, higher doses than this may be considered in view of the lower level of toxic side effects obtained with the compounds, for example in the range from 0.1 to 50 mg/kg of body weight per day or possibly even as high as described in U.S. Pat. No. 4,197,249 for the anthraquinone cancer drugs described therein, i.e. up to 200 mg/kg of body weight per day. This dosage regime may be continued for however many days is appropriate to the patient in question, the daily dosages being divided into several separate administrations if desired.

The compounds (I) are of particular value for the treatment of cancer in warm blooded animals including humans. The compounds are of interest in relation to the treatment of disseminated tumours such as leukaemias and lymphomas but more particularly of solid tumours such as various forms of sarcoma and carcinoma. Further information on dosage regimes and types of cancer to be treated may be obtained from the data on the corresponding or related compounds not containing the N-oxide group which is given in standard publications such as the ABPI Data Sheet Compendium published annually in the U.K. by Datapharm Publications Ltd., London, and in the Physicians' Desk Reference published annually in the U.S.A. by the Medical Economics Company, Inc., Oradell.

It may be advantageous to use the compounds (I) in a combined treatment, given separately or together in the same composition, with other anti-cancer agents, such as mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

In a variation of the usual procedure which relies upon the anaerobic conditions within neoplastic tissue to effect selective reduction of the N-oxide in such tissue, the selectivity as between neoplastic and normal tissue can be enhanced. Thus antibodies can be raised against tumours by conventional procedures, particularly using hybridoma technology, and linked covalently to a reductase using one of various conventional linking agents. The conjugate is administered to the patient when it localises in the body at the tumour site and the compound (I) is then administered, the action of the reductase enhancing the specificity of the action of the compound at the tumour site.

It should be appreciated that even where selective oxidation in hypoxic tissue is not playing a major role in the in vivo action of the compounds, they may still exert a valuable anti-cancer effect, for example where the compounds are reduced in the liver.

The compounds of formula (I) are also of potential value in the treatment of anaerobic bacterial infections. Representative of infectious diseases that may be treated with the compounds and compositions of the present invention include, for example, post-operative sepsis following lower gastrointestinal surgery or female urogenital surgery, pelvic inflammatory disease, ulcers, gangrene, trichomonal vaginitis, non-specific vaginitis, amoebiasis, giardiasis, periodental disease, acne and the like. The compounds may, for anti-bacterial use, be administered in the form of similar pharmaceutical compositions which are used for the anti-cancer use and at similar dosage levels.

The present invention thus includes a method suitable for aiding regression and palliation of cancer or for the treatment of an anaerobic bacterial infection, which comprises administering to a patient a therapeutically effective amount of a compound (I) as defined hereinbefore.

The invention is illustrated by the following Example.

EXAMPLE

Preparation of
9,10-bis-{N-[2-(dimethylamino-N-oxide)ethyl] aminomethyl}anthracene (1) 9,10-bis-[N-(2-Dimethylaminoethyl)aminomethyl]anthracene 1.0 g (0.0036 mol) of 9,10-dichloromethylanthracene (0.0036 mol) is refluxed for 20 minutes with 15 g of 2-dimethylaminoethylamine. The reaction mixture is added to water and the precipitate collected by filtration. The dried solid is then recrystallised from ethyl acetate to yield 0.5 g of the title compound as yellow crystals, m.p. 58°–60° C.; $\lambda_{max}$ (distilled water) (E/cm/M) 248 nm (51760), 372 nm (9030), 392 nm (8305).

(2) 9,10-bis-{N-[2-(Dimethylamino-N-oxide)ethyl]aminomethyl}, anthracene 0.13 g (0.00034 mol) of 9,10-bis-[N-(2-dimethylaminoethyl)aminomethyl]anthracene is dissolved in 5 ml of dichloromethane and cooled in an ice-bath whilst stirring. To this solution is added 0.164 g (0.00076 mol) of 3-chloroperbenzoic acid (80%) and the mixture is left for 8 hours at 0° C. protected from light. The solvent is then removed under vacuum and the residue dissolved in methanol (2 ml). This solution is subjected to flash column chromatography using a column of silica gel (60A) and a step-gradient eluting solvent of dichloromethane:methanol:28% aqueous ammonia starting with dichloromethane:methanol (50:50 v/v), followed by dichloromethane:methanol (20:80 v/v), dichloromethane:methanol (10:90 v/v) and finally methanol:28% aqueous ammonia (90:10 v/v). The last eluting fraction is collected, filtered and evaporated in vacuo to yield 0.1 g of the title compound as a yellow solid, m.p. 110°–112° C., $\lambda_{max}$ (distilled water) (E/cm/M) 250 nm (48610), 374 nm (7540), 394 nm (7390).

I claim:

1. A compound of formula (I)

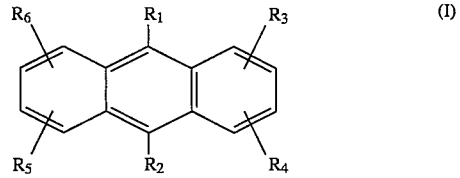

in which $R_1$ is CH=N—A—N(O)R'R" or $CH_2$—NH—

A—N(O)R'R" and $R_2$ is separately selected from hydrogen, CH=N—A—N(O)R'R" and $CH_2$—NH—A—N(O)R'R", wherein A is a $C_{2-4}$ alkylene group with a chain length between N or NH and N(O)R'R" of at least 2 carbon atoms, and R' and R" are each separately selected from $C_{1-4}$ alkyl groups and $C_{2-4}$ hydroxyalkyl and $C_{3-4}$ dihydroxyalkyl groups in which the carbon atom attached to the nitrogen atom does not carry a hydroxy group and no carbon atom is substituted by two hydroxy groups, or R' and R" together are a $C_{2-6}$ alkylene group which with the nitrogen atom to which R' and R" are attached forms a heterocyclic group having 3 to 7 atoms in the ring, and $R_3$, $R_4$, $R_5$ and $R_6$ are each separately selected from hydrogen, hydroxy, halogeno, amino, $C_{1-4}$ alkoxy and $C_{2-8}$ alkanoyloxy, the compound optionally being in the form of a physiologically acceptable salt.

2. A compound according to claim 1, in which $R_2$ is other than hydrogen.

3. A compound according to claim 1, in which $R_3$, $R_4$, $R_5$ and $R_6$ are each hydrogen.

4. A compound according to claim 1, in which A is ethylene or trimethylene.

5. A compound according to claim 1, in which R' and R" are each separately selected from $CH_3$, $CH_2CH_3$, $CH_2CH_2CH_3$, $CH_2CH_2OH$, $CH_2CH_2CH_2OH$, $CH(CH_3)CH_2OH$ and $CH_2CHOHCH_2OH$.

6. A compound according to claim 1, which contains one or two groups $CH_2$—NH$(CH_2)_n$—N(O)(CH($CH_3$)$CH_2OH)_2$ separately selected from $CH_2$—NH—$(CH_2)_n$—N(O)($CH_3)_2$, $CH_2$—NH—$(CH_2)_n$—N(O)($CH_3$)$C_2H_5$, $CH_2$—NH—$(CH_2)_n$—N(O)($C_2H_5)_2$, $CH_2$—NH—$(CH_2)_n$—N(O)($CH_2CH_2OH)_2$, $CH_2$—NH—$(CH_2)_n$—N(O)($CH_2CH_2CH_2OH)_2$, $CH_2$—NH—$(CH_2)_n$—N(O)CH($CH_3$)OH and $CH_2$—NH—$(CH_2)_n$—N(O)($CH_2CHOHCH_2OH)_2$ wherein n is 2 or 3.

7. A compound according to claim 1, in which
(1) $R_1=CH_2$—NH—A—N(O)R'R" and $R_2=R_3R_4=R_5=R_6=H$; or
(2) $R_1=R_2=CH_2$—NH—A—N(O)R'R" and $R_3=R_4=R_5=R_6=H$.

8. A compound according to claim 1, in which $R_1=R_2=CH_2$—NH—A—N(O)R'R" and $R_3=R_4=R_5=R_6=H$, with both $CH_2$—NH—A—N(O)R'R" being $CH_2$—NH—$(CH_2)_2$—N(O)($CH_3)_2$, $CH_2$—NH—$(CH_2)_2$—N(O)($C_2H_5)_2$ or $CH_2$—NH—$(CH_2)_2$—N(O)($CH_2CH_2OH)_2$.

9. A compound according to claim 1, which is 9,10-bis-{N-[2-(dimethylamino-N-oxide)ethyl]aminomethyl}anthracene.

10. A pharmaceutical composition comprising a compound of formula (I) as defined in claim 1 with a physiologically acceptable diluent or carrier.

* * * * *